(12) United States Patent
Bridges et al.

(10) Patent No.: US 9,395,290 B2
(45) Date of Patent: Jul. 19, 2016

(54) DETECTION OF REINFORCEMENT METAL CORROSION (75) Inventors: Greg E. Bridges, Winnipeg (CA); Douglas E. Thomson, Winnipeg (CA); Sharmistha Bhadra, Winnipeg (CA)

(73) Assignee: University of Manitoba, Winnipeg (CA)

( * ) Notice: Subject to any disclaimer, the term of this patent is extended or adjusted under 35 U.S.C. 154(b) by 620 days.

(21) Appl. No.: 13/695,957

(22) PCT Filed: Jun. 8, 2011

(86) PCT No.: PCT/CA2011/000679
§ 371 (c)(1),
(2), (4) Date: Jan. 16, 2013

(87) PCT Pub. No.: WO2011/153628
PCT Pub. Date: Dec. 15, 2011

(65) Prior Publication Data
US 2013/0106447 A1 May 2, 2013

Related U.S. Application Data (60) Provisional application No. 61/353,032, filed on Jun. 9, 2010.

(51) Int. Cl.
*G01R 27/08* (2006.01)
*G01N 17/04* (2006.01)
(Continued)

(52) U.S. Cl.
CPC . *G01N 17/04* (2013.01); *B60L 1/00* (2013.01); *H03H 1/00* (2013.01); *H03H 3/00* (2013.01)

(58) Field of Classification Search
CPC ........... H03H 1/00; H03H 3/00; H03H 21/00; B60L 1/00; B60L 2200/00; B60L 2210/00
USPC ........................................................ 324/700
See application file for complete search history.

(56) References Cited

U.S. PATENT DOCUMENTS 3,726,777 A  4/1973 Macur
4,861,453 A * 8/1989 Matsuoka et al. ............ 204/404
(Continued)

FOREIGN PATENT DOCUMENTS

CA          2799236      6/2011
WO     2004/010104 A2   1/2004
(Continued)

OTHER PUBLICATIONS

Andringa et al. "Unpowered wireless corrosion sensor for steel reinforced concrete" 2005. *IEEE Sensors*. pp. 155-158.
(Continued)

*Primary Examiner* — Huy Q Phan
*Assistant Examiner* — Temilade Rhodes-Vivour
(74) *Attorney, Agent, or Firm* — Mueting, Raasch & Gebhardt, P.A.

(57) ABSTRACT

Systems, devices, and/or methods for use in detection of reinforcement metal corrosion within material, such as concrete, are described. The systems, devices, and/or methods may use a passive sensor located within the material and an interrogator located outside of the material that may be used to interrogate the passive sensor and to receive a signal from the passive sensor representative of corrosion potential of reinforcement metal.

18 Claims, 8 Drawing Sheets

(51) Int. Cl.
  *B60L 1/00* (2006.01)
  *H03H 1/00* (2006.01)
  *H03H 3/00* (2006.01)

(56) References Cited

U.S. PATENT DOCUMENTS

| | | | | |
|---|---|---|---|---|
| 4,927,503 | A | * | 5/1990 | Polly .......................... 205/776.5 |
| 5,015,355 | A | * | 5/1991 | Schiessl ........................ 204/404 |
| 5,259,944 | A | * | 11/1993 | Feliu et al. .................... 204/404 |
| 5,403,550 | A | * | 4/1995 | Wietek ............................ 422/53 |
| 5,792,337 | A | * | 8/1998 | Padovani et al. ............ 205/775.5 |
| 5,942,991 | A | * | 8/1999 | Gaudreau .......... G06K 19/0717 324/337 |
| 5,964,992 | A | * | 10/1999 | Swette et al. .................. 204/404 |
| 6,806,808 | B1 | * | 10/2004 | Watters .................... G01D 5/48 340/10.41 |
| 7,034,660 | B2 | | 4/2006 | Watters et al. |
| 7,124,039 | B2 | | 10/2006 | Gadini et al. |
| 7,248,182 | B2 | | 7/2007 | Dudda et al. |
| 7,714,564 | B2 | | 5/2010 | Wright et al. |
| 7,801,626 | B2 | | 9/2010 | Moser |
| 2006/0037399 | A1 | * | 2/2006 | Brown ..................... G01H 3/12 73/580 |
| 2006/0125493 | A1 | * | 6/2006 | Subramanian ......... G01N 17/04 324/700 |
| 2007/0120572 | A1 | * | 5/2007 | Chen ...................... G01N 17/04 324/700 |
| 2008/0204275 | A1 | | 8/2008 | Wavering et al. |
| 2009/0039864 | A1 | | 2/2009 | Gordon |
| 2009/0058427 | A1 | | 3/2009 | Materer et al. |
| 2009/0128169 | A1 | * | 5/2009 | Fay ........................ G01N 17/04 324/700 |
| 2010/0198039 | A1 | * | 8/2010 | Towe ............................ 600/373 |
| 2015/0053575 | A1 | | 2/2015 | Bridges et al. |

FOREIGN PATENT DOCUMENTS

| | | |
|---|---|---|
| WO | 2004/010104 A3 | 1/2004 |
| WO | 2011/153628 | 12/2011 |

OTHER PUBLICATIONS

Apostolopoulos et al. "Consequences of steel corrosion on the ductility properties of reinforcement bar". 2008. *Construction and Building Materials*. 22(12):2316-2324.

Browne et al. 1983. Corrosion of Reinforcement in Concrete Construction. A.P. Crane, Ed., UK:Ellis Horwood Ltd. Title Page, Copyright Page, Table of Contents, pp. 193-222.

Butler et al. "Wireless passive, resonant-circuit, inductively coupled, inductive strain sensor". 2002. *Sensors and Actuators A*. 102(1):61-66.

Cabrera. "Deterioration of concrete due to reinforcement steel corrosion". 1996. *Cement and Concrete Composites*. 18(1):47-59.

Del Grosso et al. "Health monitoring for corrosion detection in reinforced concrete bridges". 2008. Bridge Maintenance, Safety, Management, Health Monitoring and Informatics—Koh & Frangopol (eds), Taylor and Francis Group, London. pp. 1532-1539.

Du et al. "In situ measurement of Cl-concentrations and pH at the reinforcing steel/concrete interface by combination sensors". 2006. *Anal. Chem*. 78(9):3179-3185.

"Embedded Corrosion Instrument" [Online]. http://www.vatechnologies.com/eciNeed.htm. Accessed Mar. 3, 2014. 2 pages.

Ervin et al. "Longitudinal guided waves for monitoring corrosion in reinforced mortar". 2008. *Measurement Science and Technology*. 19(5):055702. 19 pages.

Harpster et al. "A passive wireless integrated humidity sensor". 2002. *Sensors and Actuators A*. 95(2-3):100-107.

Horton et al. "A Varactor-Based, Inductively Coupled Wireless pH Sensor" 2011. *IEEE Sensors Journal*. 11(4):1061-1066/.

Inaudi et al. "Reinforced Concrete Corrosion Wireless Monitoring System". 2009. 4th Intl. Conference on Structural Health Monitoring on Intelligent Infracture (SHMI-4). Zurich, Switzerland. pp. 1-10.

Miller et al. "Detection and imaging of surface corrosion on steel reinforcing bars using a phase-sensitive inductive sensor intended for use with concrete". 2003. *NDT & E International*. 36(1):19-26.

Nowak et al. "A novel architecture for remote interrogation of wireless battery free capactive sensors". 2006. *Presented at the 13th IEEE International Conference on Electronics, Circuits and Systems*. 4 pages.

Ong et al. "A wireless passive embedded sensor for real time monitoring of water content in civil engineering materials". 2008. *IEEE Sensors Journal*. 8(12):2053-2058.

Ong et al. "Wireless passive resonant-circuit for monitoring food quality". 2002. *Proceedings of SPIE*. 4575:150-159.

Pasupathy et al. "Unpowered resonant wireless sensor nets for structural health monitoring" 2008. *Proc. IEEE Sensors*. pp. 697-700.

Reis et al. "Estimation of corrosion damage in steel reinforced mortar using waveguides". 2005. *ASME Journal of Pressure Vessel Technology*. 127:255-261.

Robinson et al. "Improved determination of Q-factor and resonant frequency by a quadratic curve fitting method". May 2005. IEEE Transaction on Electromagnetic Compatibility. 47(2):399-402.

Song et al. "Corrosion monitoring of reinforced concrete structures—a review" 2007. *International Journal of Electromechanical Science*. 2:1-28.

Tesche et al. "EMC analysis methods and computational models". 1997. New York: John Wiley & Sons, Inc. Title Page, Copyright Page, Table of Contents. 9 pages total.

Yeo et al. "Monitoring ingress of moisture in structural concrete using a novel optical-based sensor approach". 2006. *Journal of Physics: Conference Series*. 45:186-192.

Written Opinion, issued on Sep. 6, 2011 in related case PCT/CA2011/000679. 5 pages.

International Preliminary Report on Patentability, issued on Dec. 10, 2012, in related case PCT/CA2011/000679. 1 page.

International Search Report in related case PCT/CA2011/000679, issued on Sep. 6, 2011. 4 pages.

Ativanichayaphong et al., "Development of an Implanted RFID Impedance Sensor for Detecting Gastroesophageal Reflux," in *Proc. IEEE International Conference on RFID*, Gaylord Texan Resort, Grapevine, TX, USA, Mar. 26-28, 2007, pp. 127-133.

Ativanichayaphong et al., "An implantable batteryless wireless impedance sensor for Gastroesophageal reflux diagnosis," in *Proc. of IEEE MTT-S International Microwave Symposium Digest*, 2010, pp. 608-611.

Barron et al., "The effects of temperature on pH measurement," Technical Services Department Reagecon Diagnostics Ltd, Shannon Free Zone, County Lake, Ireland, Rep. TSP-01 Issue 1, 2005.

Bhadra et al., "Electrode potential based coupled coil sensor for remote pH monitoring," *IEEE Sensors J*., Nov. 2011;11(11):2813-2819.

Bhadra, Sharmistha "A Wireless Passive Sensor for In Vivo pH Monitoring," CMC Microsystems, TEXPO 2012; 1 Slide.

Bhadra et al., "A Wireless Passive Sensor for In Vivo pH Monitoring," CMC Microsystems, TEXPO 2012, Abstract; 2 pgs.

Bhadra et al., "Wireless Passive Sensor for pH Monitoring inside a Small Bioreactor," *IEEE Conference*, Minneapolis, MN, May 6-9, 2013; 4 pgs.

Bhadra et al., "Fluid Embeddable Coupled Coil Sensor for Wireless pH Monitoring in a Bioreactor," *IEEE Trans Instr Measur*, May 2014;63(5):1337-1346.

Bhadra et al., "A Wireless Passive Sensor for Treatment Compensated Remote pH Monitoring," *IEEE Sensors Journal*, Jun. 2013;13(6): 2428-2436.

Bhadra et al., "A Wireless Passive pH Sensor Based on pH Electrode Potential Measurement," *IEEE Conference*, Kona, HI, Nov. 1-4, 2010; 927-930; 4 pgs.

Bhadra et al., "A Wireless Passive Sensor for pH Monitoring Employing Temperature Compensation," *IEEE Conference*, Limerick, Oct. 28-31, 2011; 4 pgs; 1522-1525.

Bhadra et al., "A Wireless Passive pH Sensor for Real-Time In Vivo Milk Quality Monitoring," *IEEE Conference*, Taipei, Oct. 28-31, 2012; 4 pgs.

Bhadra et al., "Wireless Passive Sensor for Remote pH Monitoring," *J Nanotech Eng Med*, Feb. 1, 2011;2:011011-1-011011-4.

(56) References Cited

OTHER PUBLICATIONS

Bhadra, Sharmistha, "Coupled Resonant Coil Sensors for Remote Passive Monitoring Applications," Thesis submitted to the Faculty of Graduate Studies of the University of Manitoba, 2010; 149 pgs.

Dybko et al., "Assesment of water quality based on multiparameter fiber optic probe," *Sensors and Actuators B: Chemical*, Aug. 1998; 51(1-3): 208-213.

Engels et al., "Medical application of silicon sensors," *J. Phys E: Sci. Instrum*, 1983;16(10):987-994.

Frisby et al., "Development of an autonomous, wireless pH and temperature sensing system for monitoring pig meat quality," *Meat Science*, 2005;70:329-336.

Gill et al., "Investigation of thick-film polyaniline-based conductimetric pH sensors for medical applications," *IEEE Sensors J.*, May 2009; 9(5):555-562.

Grant et al., "A sol-gel based fiber optic sensor for local blood pH measurements," *Sensors and Actuators B: Chemical*, Nov. 1997; 45(1): 35-42.

Harms et al., "Bioprocess monitoring," *Current Opinion in Biotechnology*, Apr. 2002; 13(2): 124-127.

Huang et al., "A passive radio-frequency pH-sensing tag for wireless food-quality monitoring," *IEEE Sensors J.*, Mar. 2012;12(3):487-495.

Huang et al., "A flexible pH sensor based on the iridium oxide sensing film," *Sensors and Actuators*, 2011;169:1-11.

Jain et al., "A wireless micro-sensor for simultaneous measurement of pH, temperature, and pressure," *Smart Materials and Structures*, 2001;10(2):347.

Jeevarajan et al., "Continuous pH monitoring in a perfused bioreactor system using an optical pH sensor," *Biotechnology and Bioengineering*, May 2002;78(4): 467-472.

Kermis et al., "Dual excitation ratiometric fluorescent pH sensor for noninvasive bioprocess monitoring: development and application," *Biotechnology Progress*, Sep. 2002;18(5):1047-1053.

Komives et al., "Bioreactor state estimation and control," *Current Opinion in Biotechnology*, Oct. 2003; 14(5): 468-474.

Kumar et al., "Minibioreactors," *Biotechnology Letters*, Jan. 2004;26(1):1-10.

Kurzweil, "Metal oxides and ion-exchanging surfaces as pH sensors in liquids: state-of-the-art and outlook," *Sensors*, 2009; 9: 4955-4985.

Lemos et al., "Soil calcium and pH monitoring sensor system," *J. Agric. Food Chem.*, Jun. 2007;55(12): 4658-4663.

Lin, J. "Recent development and applications of optical and fiber-optic pH sensors," *Trends in Analytical Chemistry*, Sep. 2000;19(9):541-552.

Loh et al., "Inductively Coupled Nanocomposite Wireless Strain and pH Sensors," *Smart Structures and Systems*, 2008;4(5): 531-548.

Nicolaou et al., "Rapid and quantitative detection of the microbial spoilage in milk using Fourier transform infrared spectroscopy and chemometrics," *The Analyst*, Jul. 2008; 133(10): 1424-1431.

Nolan et al., "Fabrication and characterization of a solid state reference electrode for electroanalysis of natural waters with ultramicroelectrodes," *Anal. Chem.*, Mar. 1997; 69: 1244-1247.

Nopper et al., "Wireless readout of passive *LC* sensors," *IEEE Transaction on Instrumentation and Measurement*, Sep. 2010; 59(9): 2450-2457.

Ong et al., "Remote query resonant-circuit sensors for monitoring of bacteria growth: application to food quality control," *Sensors*, 2002; 2: 219-232.

Panova et al., "In situ fluorescence imaging of localized corrosion with a pH sensitive imaging fiber," *Anal. Chem.*, Apr. 1997; 69(8):1635-1641.

Papeschi et al., "An iridium—iridium oxide electrode for in vivo monitoring of blood pH changes," *Journal of Medical Engineering & Technology*, Mar. 1981;5(2):86-88.

Potyrailo et al., "Battery-free Radio Frequency Identification (RFID) Sensors for Food Quality and Safety," *J Agri Food Chem*, 2012;60:8535-8543.

Rubinstein et al., Polumer films on electrodes 4. Nafion-coated electrodes and electrogenerated chemiluminescence of surface-attached tris(2,2'-bipyridine)ruthernium(2+), *J of Amer Chem Soc*, Oct. 1980:102(21):6641-6642.

Soller et al., "Fiber optic sensing of tissue pH to assess low blood flow states," in *Proc. IEEE Sensors*, 2002:266-269.

Tsai, et al., "Noninvasive optical sensor technology in shake flasks for mammalian cell cultures," *BioProcess International*, Jan. 2012; 10(1):50-56.

Vasala et al., "A new wireless system for decentralized measurement of physiological parameters from shake flask," *Microbial Cell Factories*, Feb. 2006; 5(8):1-6.

Vuppu et al., "Economical wireless optical ratiometric pH sensor," *Meas. Sci. Technol.*, Feb. 2009; 20:045202(7pp).

Wilson and Walker, *Principles and Techniques of Biochemistry and Molecular Biology*, 7$^{th}$ ed., New York, Cambridge University Press, 2010, Cover page, title page and table of contents.

Wolthuis et al., "Development of medical fiber-optic pH sensor based on optical absorption," *IEEE Trans. Biomed. Eng.*, May 1992;39:531-537.

Yao et al., "A pH electrode based on melt-oxidized iridium oxide," *Journal of the electrochemical society*, 2001;148(4): H29-H36.

Zeng et al., "Time domain characterization of oscillating sensors: Application of frequency counting to resonance frequency determination," *Review of Scientific Instruments*, Dec. 2002;73(12): 4375-4380.

International Search Report and Written Opinion for PCT/IB2012/055477, issued by the Canadian Intellectual Property Office as the International Searching Authority, mailed Feb. 19, 2013; 10 pgs.

International Preliminary Report on Patentability for PCT/IB2012/055477, issued by the International Bureau of WIPO, mailed May 1, 2014; 8 pgs.

\* cited by examiner

DETECTION OF REINFORCEMENT METAL CORROSION

CROSS-REFERENCE TO RELATED APPLICATION

This application is the §371 U.S. National Stage of International Application No. PCT/CA2011/000679, filed 8 Jun. 2011, which claims the benefit of U.S. Provisional Patent Application Ser. No. 61/353,032 filed 9 Jun. 2010, entitled "SYSTEMS AND METHODS FOR DETECTING CORROSION OF STEEL REINFORCEMENT," each of which are incorporated herein by reference in their entireties.

BACKGROUND

The present disclosure relates generally to detection of reinforcement metal corrosion. More particularly, the present disclosure pertains to systems, devices, and methods for use in detection of corrosion, conditions for corrosion, and/or conditions favorable for corrosion of reinforcement metal (e.g., steel reinforcement within concrete structures, etc.).

A large part of civil infrastructure includes concrete reinforced with steel ("reinforced concrete"). The steel in reinforced concrete may be subject to corrosion, which is a factor in the premature deterioration of civil structures. Damage due to corrosion may reduce the service life of the infrastructure and may create safety hazards.

Ingress of Chloride (Cl—) ions into concrete is a cause of corrosion damage. When a structure is first built, bare reinforcement steel is often exposed to oxygen and water and a very thin (approximately 1 micrometer ($\mu m$)) dense layer of either metal oxide or hydroxide may be formed on the surface forming a thin passive layer. The reinforcement steel (e.g., steel bars or rods) may be protected from corrosion by this thin passive layer. Further, the highly alkaline environment of the surrounding concrete (e.g., pH value of about 12.6) may help maintain the thin passive layer on the surface of the reinforcement steel.

However, Chloride (Cl—) ions from de-icing salts often used to keep roads clear of snow and ice and from exposure to marine environment or admixtures (e.g., present at the time of concrete mixing) may permeate the concrete to reach the reinforcement steel (e.g., located at a depth below a surface of the concrete) and destroy the thin passive layer. After the thin passive layer is destroyed, corrosion of the reinforcement steel may begin.

Once corrosion begins, corrosion is self-sustaining. Rust formation (e.g., which is a corrosion product) on the outer surface of the reinforcement steel may result in an increase in the size (e.g., the cross-sectional size) of the reinforcement steel. For example, rust occupies about two to about six times the volume of original reinforcement steel, and as a result, the rust may exert stress within the concrete that cannot be supported by its limited plastic deformation. This stress may generate cracks and spalls, which subsequently may lead to the degradation of the structure and may provide new means for water and Cl— ions to reach the reinforcement steel.

Since reinforcement steel is embedded in concrete, by the time the effects of corrosion are visible on the surface of the concrete, the damage to the concrete may be severe. The estimated cost of repairing reinforced concrete structures may be greater than about $200 per square meter of exposed, damaged surface. As a result, repair, maintenance, and replacement cost of reinforced concrete often consumes a substantial amount of public spending on civil infrastructure. Further, reinforcement steel corrosion is not just an economic issue. Due to the corrosion of reinforcement steel, concrete structures may collapse potentially harming people.

Early detection of reinforcement steel corrosion may involve destructive testing of a suspected area of corrosion. However, certain nondestructive evaluation (NDE) methods and technologies exist for early detection of reinforcement steel corrosion. Most existing NDE sensing technology used for monitoring corrosion utilize a wired connection from an embedded sensor in the concrete to outside of the concrete. The installation and preparation of wired sensors for monitoring corrosion is often expensive and time consuming.

Another NDE sensing technology for early detection of corrosion of reinforcement steel utilizes embeddable wireless corrosion sensors (see, e.g., M. M. Andring a, D. P. Neikirk, N. P. Dickerson and S. L. Wood, "Unpowered wireless corrosion sensor for steel reinforced concrete," in Proc. IEEE Sensors, 2005, pp. 155-158; and P. P. Pasupathy, M. Zhuzhou, D. P. Neikirk and S. L. Wood, "Unpowered resonant wireless sensor nets for structural health monitoring," in Proc. IEEE Sensors, 2008, pp. 697-700). For example, several wireless embeddable corrosion sensors are commercially available such as, e.g., the ECI by Virginia Technologies, Inc. (see, e.g., "Embedded Corrosion Instrument,"[Online]. Available: http://www.vatechnologies.com/eciNeed.htm. [Accessed: Oct. 5, 2009]) and the concrete corrosion sensor by RocTest (see, e.g., "Concrete Corrosion sensor," [online]. Available: http://www.roctest.com/modules/AxialRealisation/img_repository/files/documents/SensCore-161010.pdf. [Accessed: Jan. 16, 2010]).

Such wireless corrosion sensors, however, often require a local power source (e.g., a battery) for electronics in the sensor, which may negate an advantage of using a wireless sensor because the local power source may require frequent recharging or replacement. Further, wireless corrosion sensors are often expensive.

The tendency of reinforcement steel to corrode in concrete may be indicated by a potential it develops in contact with the concrete environment, which may be referred to as "corrosion potential." Corrosion potential can provide information for corrosion probability and may be affected by a number of factors, which include polarization by limited diffusion of oxygen, concrete porosity, and the presence of a highly resistive layer. One wired NDE method available for corrosion monitoring, open circuit potential measurement, measures the corrosion potential of reinforcement steel with respect to a reference electrode (see, e.g., H. Song and V. Saraswathy, "Corrosion monitoring of reinforced concrete structures—a review," International Journal of Electrochemical Science, vol. 2, pp. 1-28, January 2007).

SUMMARY

The disclosure herein relates to a passive embeddable sensor that can detect the corrosion potential of reinforcement metal with respect to a reference metal, and thus, may be used for corrosion monitoring. One exemplary system described herein may include an embedded wireless passive sensor that is based on a LC coil resonator, where the resonant frequency changes with respect to a corrosion potential of the reinforcement metal to be monitored. In the sensor, an inductive coil may be connected in parallel with a varactor and a pair of corrosion electrodes. The first corrosion electrode may be a reinforcement metal sensing electrode and the second corrosion electrode may be a reference electrode (which is immune to corrosion). Both of the corrosion electrodes may be embedded in the material to be monitored (e.g., concrete, etc.). A voltage change across the electrodes due to the variation of corrosion potential of reinforcement steel may change the capacitance of the varactor, and thus, shift the resonant frequency of the sensor. The resonant frequency may be monitored remotely by an interrogator coil inductively coupled to the sensor coil.

One exemplary system for detecting corrosion of metal within material (e.g., concrete) may include a sensor portion locatable within the material and an interrogator portion locatable outside of the material. The sensor portion may include reinforcement metal (e.g., steel), reference metal (e.g., stainless steel), and passive sensing circuitry electrically coupled to the reinforcement metal and the reference metal. The passive sensing circuitry (e.g., encapsulated by polymer) may be configured to measure a potential between the reinforcement metal and the reference metal and may be further configured to wirelessly transmit a signal representative of a corrosion potential of the reinforcement metal based on the potential between the reinforcement metal and the reference metal when energized. The interrogator portion may include interrogating circuitry configured to wirelessly transmit energy to the sensing circuitry of the sensor portion and to wirelessly receive the signal representative of the corrosion potential from the sensing circuitry of the sensor portion.

One exemplary device for detecting corrosion of metal within material (e.g., concrete) may include reinforcement metal, reference metal (e.g., stainless steel), and passive sensing circuitry (e.g., encapsulated by polymer) electrically coupled to the reinforcement metal (e.g., steel) and the reference metal. The sensing circuitry may be configured to measure a potential between the reinforcement metal and the reference metal and may be further configured to wirelessly transmit a signal representative of a corrosion potential of the reinforcement metal based on the potential between the reinforcement metal and the reference metal when energized by an interrogator portion locatable outside of the material.

One exemplary method of detecting corrosion of metal within material (e.g., concrete) may include locating a sensor portion within material (e.g., the sensor portion of the exemplary system described herein) and locating an interrogator portion (e.g., the interrogator portion of the exemplary system described herein) outside of the material proximate the sensor portion. The exemplary method may further include wirelessly transmitting energy from the interrogator portion to the sensor portion and wirelessly transmitting a signal representative of a corrosion potential of the reinforcement metal from the sensor portion to the interrogator portion based on the potential between the reinforcement metal and the reference metal.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-8. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Figure 1:
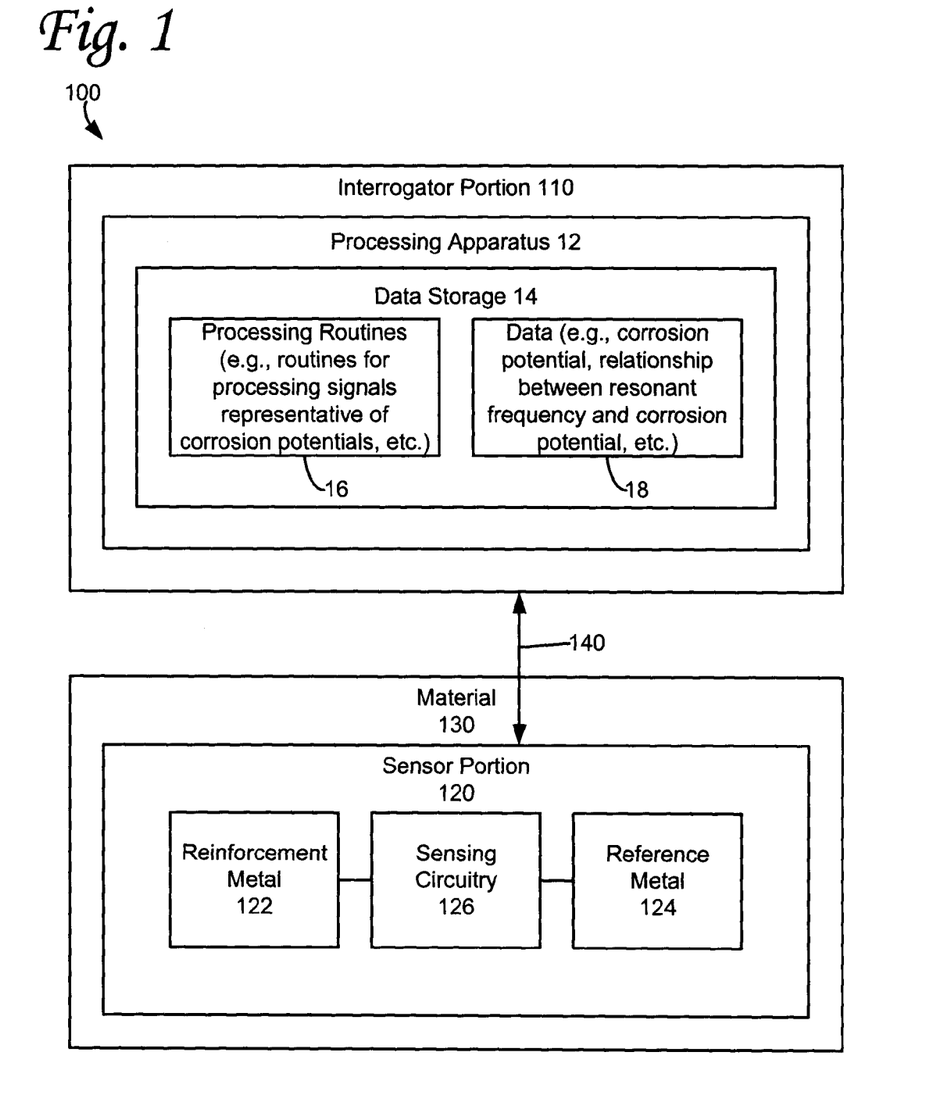
FIG. 1 is a block diagram depicting an exemplary system for use in detection of reinforcement metal corrosion.

An exemplary system 100 for use in detecting the corrosion of reinforcement metal (e.g., reinforcement steel) is depicted in FIG. 1. Generally, the system 100 includes an interrogator portion (block 110) and a sensor portion (block 120). Although the interrogator portion (block 110) and the sensor portion (block 120) are described herein as being "portions" of system 100, it is to be understood that each of the interrogator portion (block 110) and the sensor portion (block 120) may also be described herein as being "devices," such as an interrogator device (block 110) and a sensor device (block 120). The sensor portion (block 120) may be located within a material (block 130), e.g., embedded within concrete. The interrogator portion (block 110) may be used in conjunction with the sensor portion (block 120) (e.g., being located outside of the material (block 130) but still proximate to the sensor portion (block 120)).

The interrogator portion (block 110) (e.g., a handheld or mobile device, a portable device, etc.) includes interrogating circuitry configured to wirelessly transmit energy and to wirelessly receive data signals, which includes processing apparatus (block 12). The interrogating circuitry may include an interrogator coil operable to be inductively coupled to a coil of the sensor portion (block 120) to energize the sensor portion (block 120) and to receive signals from the sensor portion (block 120). Exemplary embodiments of interrogating circuitry of the interrogator portion (block 110) are further described herein with reference to interrogator portion 310 of FIG. 3.

Figure 2:
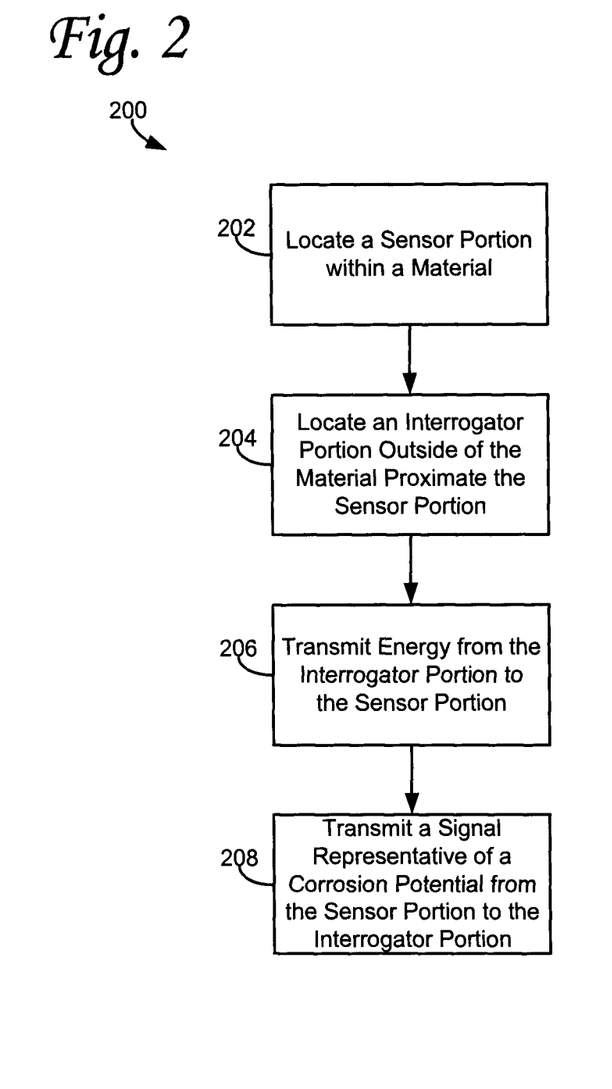
FIG. 2 depicts a general block diagram of an exemplary method for use in detection of reinforcement metal corrosion, e.g., using the exemplary system of FIG. 1

The processing apparatus (block 12) may include data storage (block 14), which allows for access to processing programs or routines (block 16) and one or more other types of data (block 18) that may be employed to carry out the illustrative methods, e.g., at least a portion of method 200 as shown generally in the block diagram of FIG. 2.

Data (block 18) may include, for example, data representative of corrosion potential (e.g., data correlating resonant frequency of a sensor portion, to corrosion potential, etc.), one or more processing programs or routines employed according to the present disclosure (e.g., calculations, formulas, interrogation programs, time-gated interrogation programs, swept-frequency interrogation programs, etc.), results from one or more processing programs or routines employed according to the present disclosure (e.g., corrosion potentials, etc.), or any other data that may be necessary for carrying out the one or more methods and processes described herein.

The exemplary methods and processes described herein may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other methods and/or processes as described herein or as would be applied in a known fashion.

The program used to implement the exemplary methods and processes described herein may be provided using any programmable language, e.g., a high level procedural and/or object orientated programming language that is suitable for communicating with a computer system. Any such programs may, for example, be stored on any suitable device, e.g., a storage media, readable by a general or special purpose program, computer or a processor apparatus (e.g., a field programmable gate array) for configuring and operating the computer when the suitable device is read for performing the methods and/or processes described herein. In other words, in at least one embodiment, the interrogator portion (block 110) may be implemented using a computer readable storage medium, configured with a computer program, where the storage medium so configured causes the computer to operate in a specific and predefined manner to perform functions described herein.

The processing apparatus (block 12) may be, for example, any fixed or mobile computer system (e.g., a personal computer, minicomputer, handheld computer, etc.). The exact configuration of the computing apparatus is not limiting and essentially any device capable of providing suitable computing capabilities and control capabilities (e.g., control the interrogator portion to interrogate the sensor portion to acquire data, such as data related to the corrosion potential of reinforcement metal) may be used. Further, various peripheral devices, such as a computer display, touchscreen, mouse, keyboard, memory, and printer, are contemplated to be used in combination with processing apparatus (block 12) of the data storage (block 14).

The sensor portion (block 120) includes reinforcement metal (block 122) (e.g., at least one piece of the metal of the same or similar type (i.e., a proxy), such as steel, steel alloy, etc., used to reinforce the material (block 130) within which the sensor portion (block 120) is located), reference metal (block 124) (e.g., at least one piece of metal that is less reactive than the reinforcement metal (block 122) such as stainless steel), and passive sensing circuitry (block 126) electrically coupled to the reinforcement metal (block 122) and the reference metal (block 124) (e.g., electrically coupled to each using insulated wires). The sensing circuitry (block 126) (e.g., analog and/or digital hardware, software, etc.) may be configured to measure a potential between the reinforcement metal (block 122) and the reference metal (block 124) (e.g., using various analog and/or digital circuitry, etc.). More specifically, the sensing circuitry (block 126) may utilize a low leakage, low dielectric loss variable capacitor (e.g., such as a varactor diode) to measure a potential between the reinforcement metal (block 122) and the reference metal (block 124). In effect, the reinforcement metal (block 122) and the reference metal (block 124) act as "corrosion detection electrodes," and may be referred to as such herein.

In at least one embodiment, the sensing circuitry (block 126) is encapsulated by a material (e.g., a polymer, etc.) to, e.g., hermetically seal the sensing circuitry (block 126) to protect it from moisture ingress.

The passive sensing circuitry (block 126) may be defined as being "passive" because it does not include a power source. In one or more embodiments, the passive sensing circuitry (block 126) includes an inductive loop coupled to a capacitor that changes capacitance based on the potential between the reinforcement metal and the reference metal. Further, the passive sensing circuitry (block 126) may be further configured to wirelessly transmit signals (e.g., to the interrogator portion (block 110) as depicted by line 140) representative of a corrosion potential of the reinforcement metal (block 122) based on the potential measured between the reinforcement metal (block 122) and the reference metal (block 124) after being energized (e.g., wirelessly energized by the interrogator portion (block 110) as depicted by line 140). Exemplary embodiments of sensing circuitry (block 126) of the sensor portion (block 120) are further described herein with reference to sensor portion 320 of FIG. 3.

The sensing circuitry (block 126) may be configured such that the resonant frequency of the wirelessly transmitted signals (e.g., one or more signals transmitted to the interrogator portion (block 110)) will shift in response to the potential between the reinforcement metal (block 122) and the reference metal (block 124). As such, the corrosion potential of the reinforcement metal (block 122) may be related to the resonant frequency of the signal transmitted from the sensing circuitry (block 126) after being energized.

In one or more embodiments, the passive sensing circuitry (block 126) of the sensor portion (block 120) may be configured to wirelessly transmit the signal representative of the corrosion potential after a selected period of time has elapsed following the energization of the sensor portion (block 120). The selected time period may be greater than or equal to about 1 millisecond (ms), about 2 ms, about 5 ms, about 10 ms, about 15 ms, etc., and less than or equal to about 50 ms, about 40 ms, about 30 ms, about 20 ms, about 15 ms, etc. In other words, the sensor portion (block 120) may be time-gated having at least two phases that are consecutive to one another, e.g., an electrical charging or energizing phase and a signal transmitting phase. Further, in turn, the interrogating circuitry of the interrogator (block 110) may be configured to wirelessly receive signals from the passive sensing circuitry (block 126) after the selected period of time has elapsed following the energization of the sensor portion (block 120). In other words, the interrogator portion (block 110) may also be time-gated having at least two phases that are consecutive to one another, e.g., an electrical charging or energizing phase and a signal receiving phase that occurs either directly or after a selected period of time after the end of the electrical charging or energizing phase.

Exemplary methods and devices that may use time-gated wireless transmission of energy and/or data may be described in S. Bhadra, E. Thompson, B. Kordi, G. E. Bridges and D. J. Thomson, "Coupled resonant coil sensors with increased interrogation distance," presented at the 5th International Conference on Bridge Maintenance, Safety and Management, Philadelphia, July 2010, which is incorporated herein by reference in its entirety.

The interrogator portion (block 110) (e.g., the processing apparatus (block 12), the interrogating circuitry, etc.) may be configured to generate a corrosion potential value representative of the corrosion potential of the reinforcement metal (block 122) based on the resonant frequency of the signal representative of the corrosion potential. For example, the interrogator portion (block 110) may analyze the signals from the passive sensing circuitry (block 126) and determine the resonant frequency of the sensor portion (block 120). From the resonant frequency, the corrosion potential of the reinforcement metal (block 122) may be generated, which is further described herein with reference to FIGS. 5-7.

In at least one embodiment, the interrogator portion (block 110) may sweep a range of frequencies (e.g., using a swept source) and measure the response from the sensor portion (block 120) for each frequency to determine the resonant frequency. The resonant frequency is the frequency that provides the greatest response signal (e.g., voltage) returned from the sensor portion (block 120).

In other words, the interrogator portion (block 110) may iteratively interrogate the sensor portion (block 120) through a range of frequencies (e.g., using a swept source) to determine the resonant frequency of the sensor portion (block 120). Further the interrogator portion (block 110) may interrogate the sensor portion through a range of frequencies in a time-gated process, e.g., using a time-gated swept source. For example, the interrogator portion (block 110) may interrogate the sensor portion (block 120) at particular frequency within a range of frequencies for a selected period to time. After the selected period of time has expired, the interrogator portion (block 110) may stop transmitting energy at the particular frequency and may sense the signals from the sensor portion (block 120). Further, after the interrogator portion (block 110) has sensed the signals (e.g., representative of corrosion potential) from the sensor portion (block 120), the interrogator portion (block 110) may again interrogate the sensor portion (block 120) at another frequency, and again sense the signals from the sensor portion (block 120) until the resonant frequency for the sensor portion (block 120) is determined (or, e.g., the range of frequencies is expired).

An exemplary method 200 for use in detection of corrosion of reinforcement metal is depicted in FIG. 2. One will recognize that one or more of the processes or functions described herein may be carried out using one or more programs or routines, and/or any other components of the system described herein. Generally, the method 200 includes locating a sensor portion (block 120) within a material (block 130) (e.g., concrete) 202, and locating an interrogator portion (block 110) outside of the material (block 130) proximate the sensor portion (block 120) 204. In at least one embodiment, the sensing circuitry (block 126) (e.g., at least portion of the sensing circuitry (block 126) used to receive energy from and transmit data to the interrogator portion 110) of the sensor portion (block 120) may be located from about 1 centimeters (cm) to about 10 cm below a surface of the material.

The interrogator portion (block 110) and the sensor portion (block 120) may need to be located within a selected range of distance from one another for proper transmission of data, e.g., data related to the corrosion potential of the reinforcement metal (block 122) of the sensor portion (block 120). In at least one embodiment, the interrogator portion (block 110) and the sensor portion (block 120) may be located about 5 cm to about 30 cm apart from one another such that the sensor portion (block 120) may be interrogated by the interrogator portion (block 110).

The method 200 further includes wirelessly transmitting energy (e.g., inductively) from the interrogator portion (block 110) to the sensor portion (block 120) 206 and wirelessly transmitting a signal representative of a corrosion potential of the reinforcement metal (block 122) from the sensor portion (block 120) to the interrogator portion (block 110) 208. The signal representative of the corrosion potential is based on a potential between the reinforcement metal (block 122) and the reference metal (block 124).

In one or more embodiments, the process step of wirelessly transmitting the signal representative of the corrosion potential from the sensor portion (block 120) 208 occurs (e.g., after a selected period of time has elapsed) following energization of the sensor portion (block 120) by the wirelessly transmitted energy from the interrogator portion (block 110) 206. In other words, the wirelessly transmitting the signal representative of the corrosion potential from the sensor portion (block 120) to the interrogator portion (block 110) 208 may be time-gated as described herein.

In at least one embodiment, the signal representative of corrosion potential may be processed by the interrogator portion (block 110) to generate or yield a corrosion potential of the reinforcement metal (block 122) of the sensor portion (block 120) (e.g., the interrogator portion (block 110) may use look-up table, or any other correlation process, predetermined data, or algorithm such as a curve fitting algorithm, to determine a corrosion potential of the reinforcement metal (block 122) of the sensor portion (block 120)). In at least another embodiment, the signal representative of corrosion potential may be stored or saved by the interrogator portion (block 110) to be used by another computing device to generate a corrosion potential of the reinforcement metal (block 122) of the sensor portion (block 120). In at least another embodiment, the signal representative of corrosion potential may be stored or saved by the interrogator portion (block 110) and a user may analyze and use the information to determine a corrosion potential of the reinforcement metal (block 122) of the sensor portion (block 120). In one or more embodiments, the signal representative of corrosion potential, or the generated corrosion potential itself, may be referred to as an "output" of the method 200. The "output" (e.g., one or more signals, one or more values, a digital file, a file in user-readable format, etc.) of the systems, devices, and/or methods described herein may be analyzed by a user, used by another machine that provides output based thereon, etc.

A digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by processing apparatus (block 12) described herein.

Also, as described herein, a file in user-readable format may be any representation of data (e.g., ASCII text, binary numbers, hexadecimal numbers, decimal numbers, audio, graphical) presentable on any medium (e.g., paper, a display, sound waves, etc.) readable and/or understandable by a user.

Generally, the methods and systems as described herein may utilize algorithms implementing standardization algorithms, comparison algorithms, vector mathematics, and/or any processing that may be used to generate a corrosion potential (e.g., from the signal representative of corrosion potential, etc.).

Figure 3:
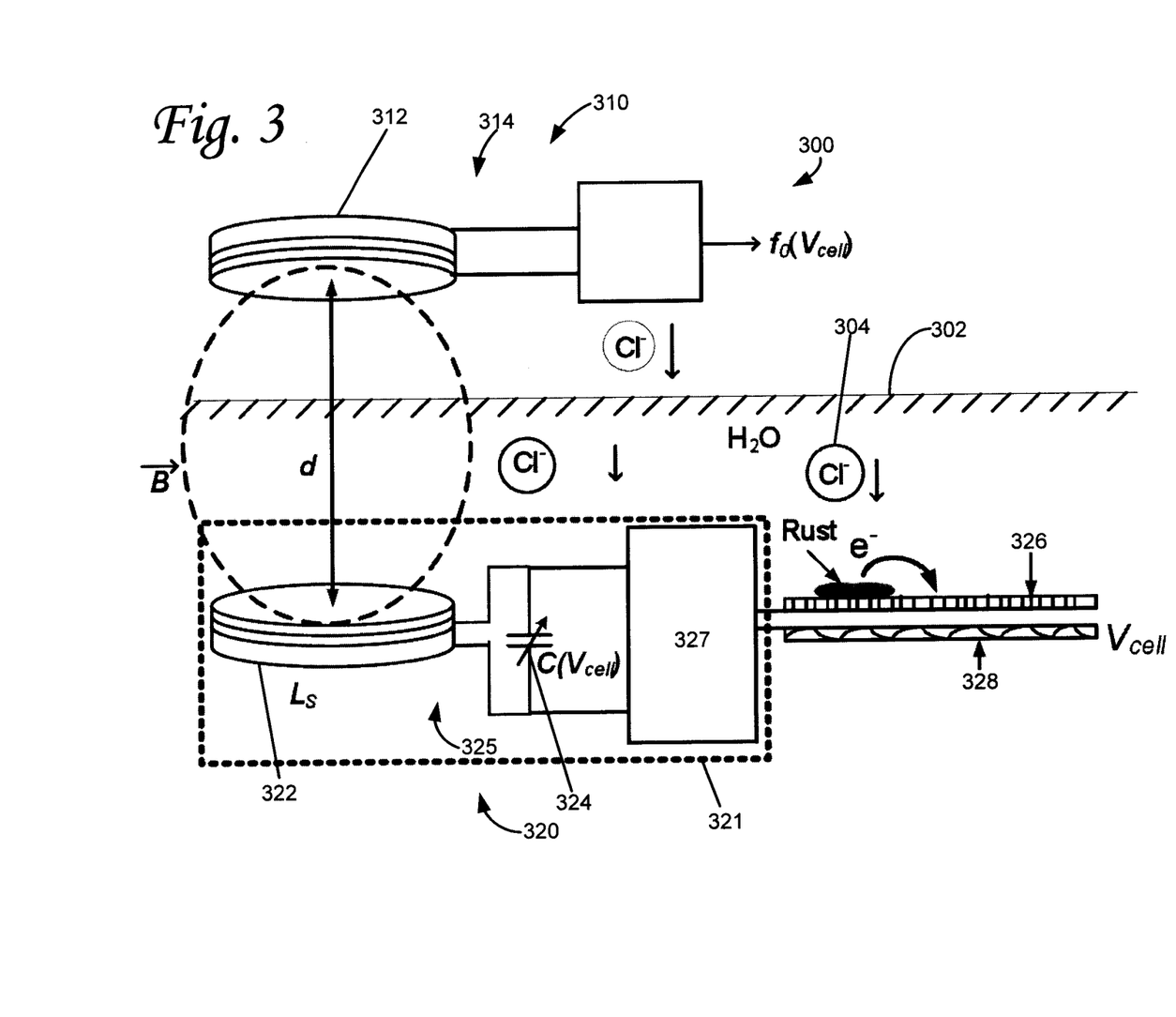
FIG. 3 is a graphical depiction of the exemplary system of FIG. 1.

A more detailed depiction of an exemplary system 300 for use in the detection of corrosion of reinforcement metal is shown in FIG. 3. The system 300 includes an interrogator portion 310 located outside, or external, to material 302 (e.g., concrete, etc.) and a sensor portion 320 located inside, or internal, to material 302. As an exemplary precursor to corrosion, Cl⁻ ions 304 are shown in FIG. 3 breaching the surface of the material 302 and moving into the material 302.

In the sensor portion 320, an inductive sensor coil 322 is connected in parallel with a voltage controlled capacitor 324 (e.g., a varactor) and a pair of corrosion sensing electrodes to form a resonant sensing circuit 325. The resonant sensing circuit 325 may be encapsulated by a casing or sealing 321 to, e.g., protect the circuit from the environment. The pair of corrosion electrodes may include a reinforcement steel sensing electrode 326 and a stainless steel reference electrode 328.

$L_S$ is the inductance of the sensor coil 322, $C(V_{cell})$ is the capacitance of the resonant sensing circuit 325, and $V_{cell}$ is the voltage developed across the corrosion sensing electrodes 326, 328 when embedded in concrete. The capacitance, $C(V_{cell})$, changes in response to the low frequency change of $V_{cell}$. The sensor coil and capacitor form the resonant sensing circuit 325 with a resonant frequency, $f_0$, approximately given by $$f_0 = \frac{1}{2\pi\sqrt{L_S C(V_{cell})}}. \tag{1}$$

An interrogator coil 312 of the interrogator portion 310 may be inductively coupled to sensor coil 322 of the sensor portion 320, and may be used to track the resonant frequency of the resonant sensing circuit 325 of the sensor portion 320, e.g., using interrogation circuitry 314. In the resonant sensing circuit 325, the resonant frequency may be directly related to the potential (e.g., voltage) developed across the pair of corrosion sensing electrodes 326, 328.

Figure 4:
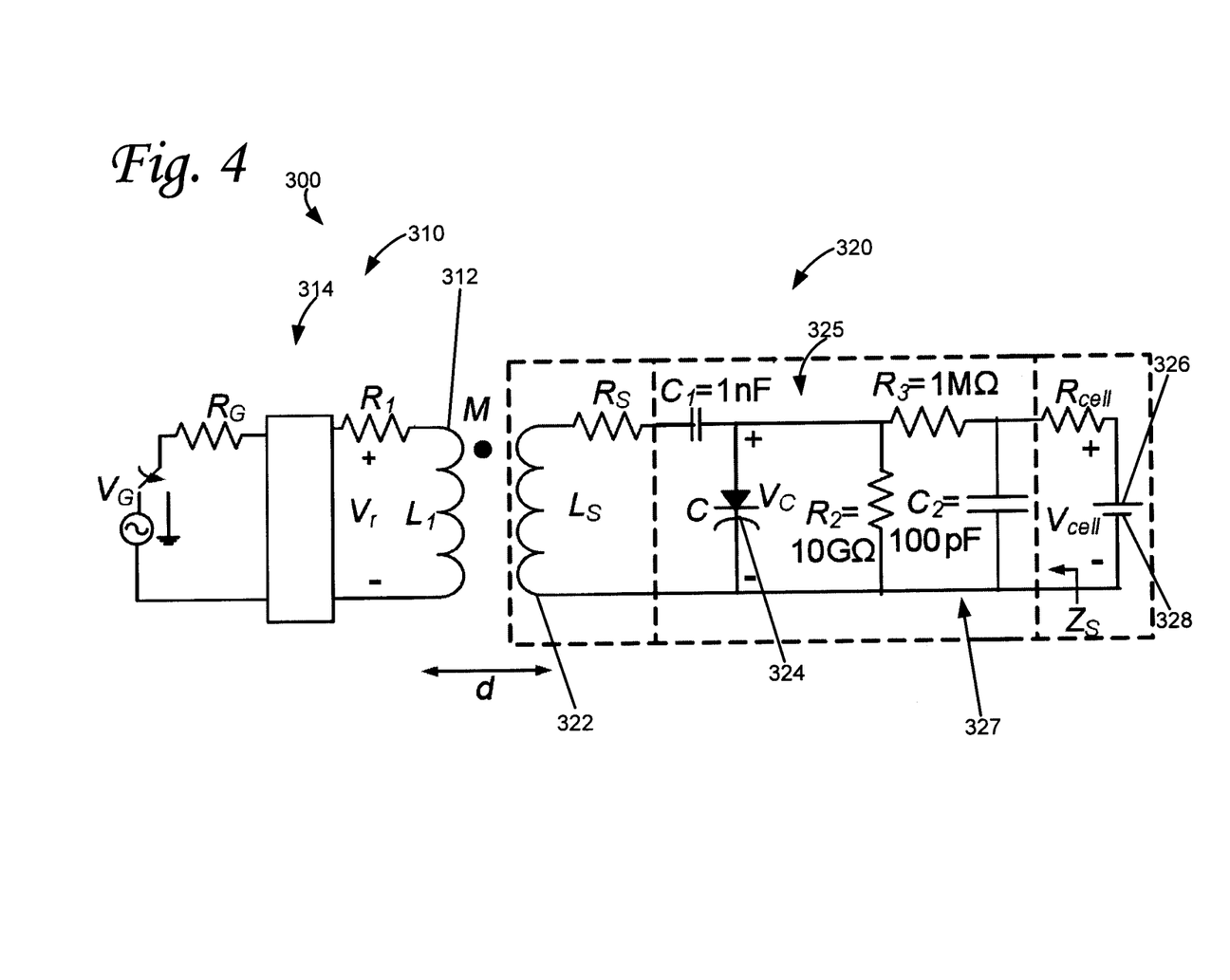
FIG. 4 is a circuit diagram of the exemplary system of FIG. 3.

An equivalent circuit diagram 350 of the exemplary system 300 of FIG. 3 is shown in FIG. 4. In the circuit diagram 350, $L_S$ and $R_S$ are the series inductance and resistance of the sensor coil 322, respectively, and $L_1$ and $R_1$ are the series inductance and resistance of the interrogator coil 312, respectively. M is the interrogator-sensor coil coupling factor. C is the small signal junction capacitance of the voltage dependent capacitor 324 (e.g., varactor) in the sensing circuit 325.

In the reverse bias state, C is approximated by $$C(V_c) = C_0(1 - V_C/\phi)^{-1/2} \tag{2}$$

where $C_0$ is the junction capacitance at zero bias, $\phi$ is the junction built in potential and $V_C$ is the bias voltage applied across the voltage dependent capacitor 324. $R_{cell}$ is the cell resistance developed at the pair of corrosion electrodes 326, 328 when embedded in the concrete 302. In the sensing circuit 325, $R_3$ and $C_2$ act as a low pass filter 327 so that the resonator is sensitive to low frequency variations in the pH electrode potential. For a small source oscillation amplitude, small M, and $R_{cell} \ll (R_2+R_3)$, $V_C \cong V_{cell}$. Assuming the losses are small and $C_1 \gg C(V_{cell})$, the corrosion potential of reinforcement steel 326 with respect to the reference steel 328, which is indicated by $V_{cell}$, can be monitored by obtaining the resonant frequency of the sensor portion 320. In at least one embodiment, the sensor portion 320 may have a high DC input impedance, $Z_s > 10$ GΩ, which may prevent galvanic corrosion.

A time-domain gating method may be used for the interrogation of the weakly coupled sensor coil (see, e.g., S. Bhadra, E. Thompson, B. Kordi, G. E. Bridges and D. J. Thomson, "Coupled resonant coil sensors with increased interrogation distance," presented at the 5th International Conference on Bridge Maintenance, Safety and Management, Philadelphia, July 2010, which is incorporated herein by reference in its entirety). For example, the interrogator coil 312 may be excited at a specified frequency by an energy source and energy therefrom may be coupled to the sensor coil 322 of the sensor portion 320. The energy source may then be ceased, and the response from the sensor portion 320, which may now be at its resonant frequency, may be monitored. The time-domain gating may be advantageous because it may eliminate a direct response of the interrogator coil 312 and the exciting signal. This results in a measurement dominated by the response of the sensor coil 322 thereby enabling detection of the sensors coil's 322 response more precisely at an extended separation distance. In other words, the time-domain gating may allow the response to the sensor coil 322 to be unperturbed by the energizing process. The voltage response developed at the interrogator coil 312 in receive mode can be expressed by $$V_r \cong \frac{\omega_0 \omega M^2 R_G}{(Z_T Z_R + \omega^2 M^2) Z_R}\bigg|_{\omega_0} V_G \tag{3}$$

where $Z_T \cong [R_S + j\omega C_1)^{-1} + (j\omega C + (((R_2+R_3)/(R_2 * R_3)))^{-1}]$ is the total sensor impedance, and $Z_R = (R_G + R_1 + j\omega L_1)$ is the interrogator impedance. In order to determine the resonant frequency, the source frequency, $\omega$, is swept near $\omega_0$ and the maximum received signal, $V_r$, may be obtained using a peak fitting algorithm. For an interrogator coil with a self-resonant frequency much greater than $\omega_0$ and for small losses, this may occur at $\omega \approx \omega_0$. In at least one embodiment, the source frequency may be swept (e.g., increased or decreased) in selected increments (e.g., in increments or decrements equal to about 0.1% of the starting resonant frequency).

A prototype embeddable sensor portion 320 was constructed by hermetically sealing the sensor coil 322 and the sensing circuit 325 in a plastic cylinder. In this prototype, the sensor coil 322 was 8.4 cm in diameter and made of 19 turns of insulated wire of 0.55 mm diameter, producing $L_S = 68.53$ pH and $R_S = 10.52 \Omega$. The sensing circuit 325 was fabricated on a 2.7 cm×1 cm printed circuit board with surface mount capacitors and resistors. The voltage controlled capacitor 324 (NXP BB202) in the sensing circuit 325 had a junction capacitance that varied in the range of 35.04 pF-22.95 pF for reverse bias voltages between 0-1V, respectively. The reinforcement steel 326 was 20 cm long with 1.2 cm diameter, and the reference stainless steel 328 was 20 cm long and 2.4 cm wide with negligible thickness. Since stainless steel has a higher reduction potential than reinforcement steel, the reinforcement steel 326 and the reference stainless steel 328 were connected to the positive and negative ends of the sensing circuit 325, respectively, so that the voltage developed across the reinforcement steel 326 and the reference stainless steel 328 sets the voltage dependent capacitor 324 in reverse bias state. Wires connecting the sensing circuit 325 to the electrodes 326, 328 were extended out of the hermetically-sealed plastic cylinder 321. The points where the wires extended out of the cylinder 321 were sealed properly with epoxy. The sensor portion 320 was designed to have a resonant frequency, $f_0$, near 3.4 megahertz (MHz).

A prototype interrogator portion 310 included an interrogator coil 312 that was 5.1 cm in diameter and constructed of 5 turns of insulated copper wire of a 1.2 millimeter (mm) diameter, producing $L_1$=2.35 µH, $R_1$=334.13 mΩ and a self-resonant frequency, $f_{res}$=28.32 MHz.

A programmable signal generator (Stanford Research Systems DS345) was used in the interrogator portion 310 to provide a swept frequency signal to the interrogator coil 312. The source amplitude, $V_G$ was set to 200 mVpp. Switching between transmit and receive mode was done using high isolation SPDT switches (ZASW-2-50DR+). A pulse generator (Quantum Composers Model 9618) provided the controlling signals for the switches. An RF lock-in amplifier (Stanford Research Systems SR844) was used for measuring the response. A computer program, developed in Labview, controlled the swept frequency of the signal generator, and recorded the response from the lock-in-amplifier through the General Purpose Interface Bus. Thus, by sweeping the frequency and measuring the response, the resonant peak of the sensor was determined using a quadratic curve-fitting algorithm (see, e.g., M. P. Robinson and J. Clegg, "Improved determination of Q-factor and resonant frequency by a quadratic curve fitting method," IEEE Transaction on Electromagnetic Compatibility, vol. 47, no. 2, pp. 399-402, May 2005, which is incorporated by reference herein in its entirety).

Figure 5:
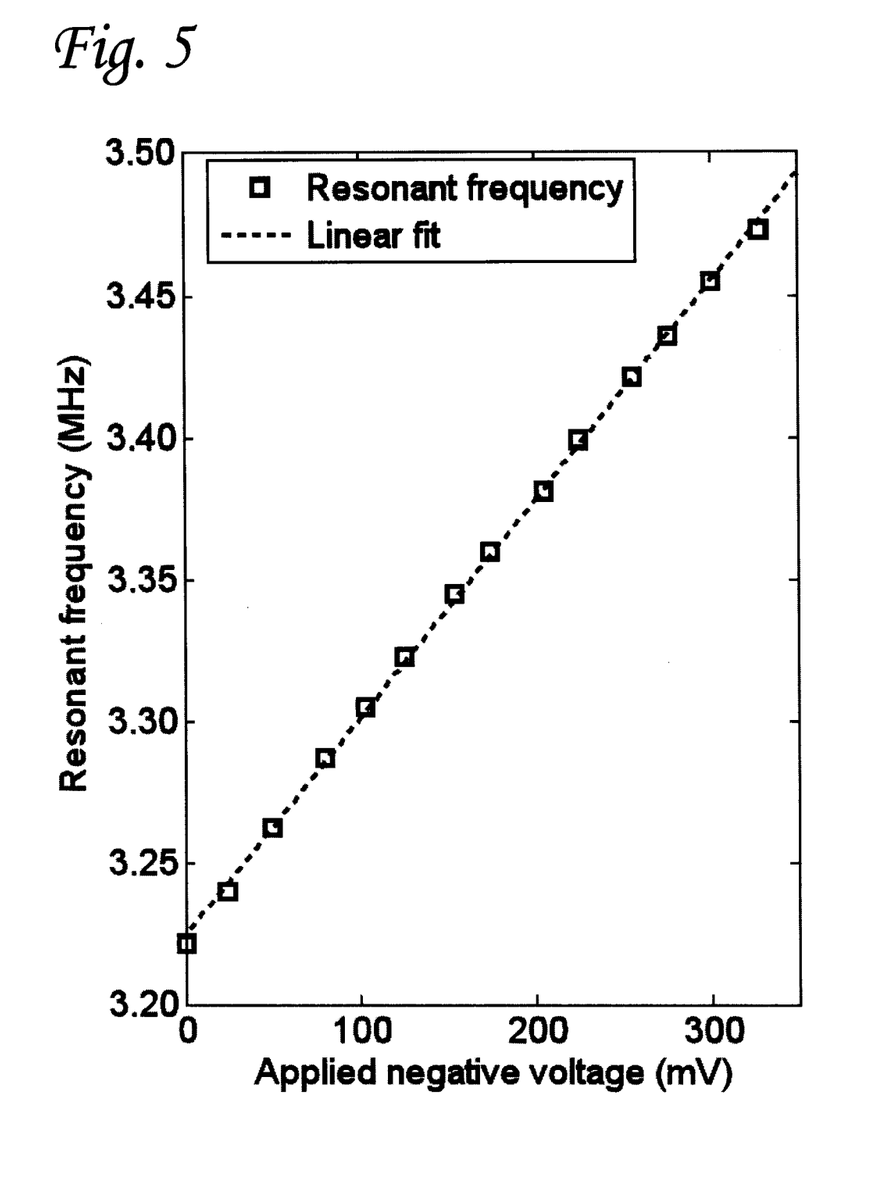
FIG. 5 is a graph of resonant frequency versus negative voltage directly applied to an exemplary sensor portion, e.g., of the exemplary system of FIG. 3.

Initially, a DC voltage was applied directly to the sensing circuit 325 of the sensor portion 320 using a power supply, and the sensor coil 322 was aligned concentrically with the interrogator coil 312 of the sensor portion 320 with a separation distance d=12 cm, and the resonant frequency, $f_0$, of the sensor portion 320 was measured for different applied negative voltages, V, as shown in FIG. 5 (e.g., a calibration curve). A linear fit may be given by $$f_0(\text{MHz})=0.00076\,V(\text{mV})+3.2249 \quad (4)$$

over the 0-330 negative voltage range, which provides a slope of 0.76 kHz/mV with a maximum deviation of less than 3.3 kHz from linear-fit (e.g., corresponding to a deviation of less than 4.3 mV). The error from the linear fit may result from a nonlinear relationship between C and $V_C$ and a higher order parasitic. Further, the source impedance in the calibration procedure was very small, whereas the reinforcement steel and reference stainless steel may have a larger source impedance.

An accelerated corrosion test was performed with an experimental setup using the prototype system 300 to detect reinforcement steel corrosion. The corrosion sensing electrodes 326, 328 along with the sealed cylinder 321 encapsulating the sensor coil 322 and sensing circuit 325 of the sensor portion 320 were embedded in a 17 cm×15 cm×18.5 cm mortar specimen. Mortar was used because its mechanical behavior is similar to concrete, and its porous nature allows $Cl^-$ ions and water to permeate the mortar quickly, which accelerated the corrosion of the reinforcement steel. The mortar specimen was made from Quickrete mason mix (type S mortar, no. 1136).

First, the corrosion sensing electrodes 326, 328 along with the sealed cylinder 321 were placed in a plastic formwork. After thoroughly mixing 2.612 kilograms (kg) of mason mix with 402 grams (gm) of water, the mortar was placed in the formwork. The reinforcement steel/reference stainless steel pair was embedded to a depth of 14.5 cm. To guard against crevice corrosion (e.g., corrosion originating where the reinforcement steel 326 exited the mortar specimen), the reinforcement steel 326 was painted with nitrile rubber at the end and in the region where it exits from the mortar specimen. The distance between the corrosion sensing electrodes 326, 326 was 1.2 cm. The distance from the center of the sensor coil 322 to the mortar specimen surface was 2 cm. After 10 days, the mortar specimen was taken out of the formwork and air cured for 14 days. After air curing, the mortar specimen was submerged in tap water for 3 days, and then in 5% NaCl solution for 11 days.

The resonant frequency of the sensor portion 320 was monitored continuously and the voltage developed across the corrosion sensing electrodes 326, 328 was also monitored continuously (e.g., directly from the corrosion sensing electrodes 326, 328 to provide a baseline to compare to the resonant frequency data of the sensor portion 320). The sensor coil 322 was aligned concentrically with the interrogator coil 312 with a separation distance of 12 cm (i.e., d=12 cm) or 16 cm (i.e., d=16 cm).

Figure 6:
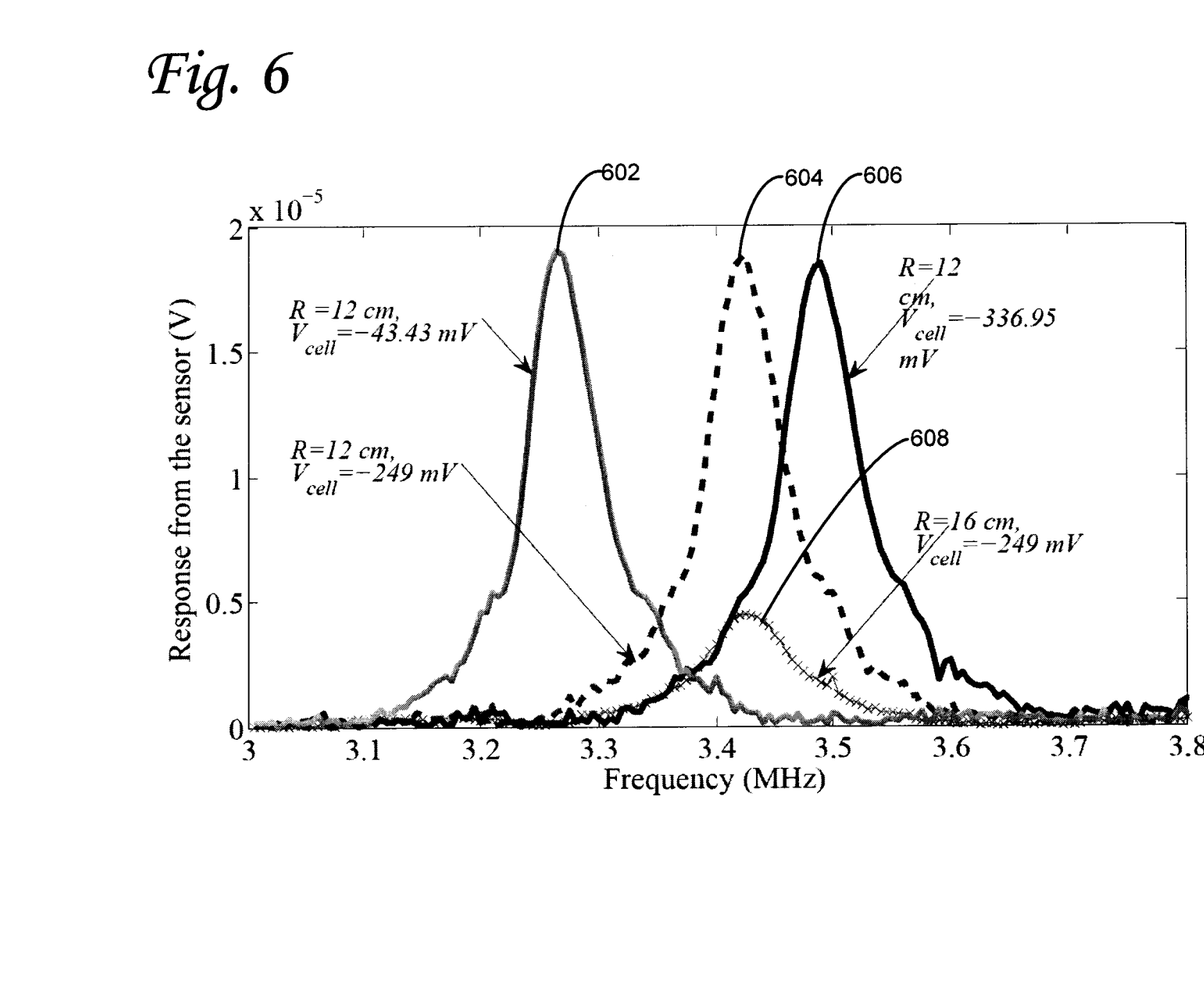
FIG. 6 is a graph of a frequency response of an exemplary sensor portion, e.g., of the exemplary system of FIG. 3.

The frequency response of the sensor portion 320 as measured by the time-domain gating method for four different voltages 602, 604, 606, 608 developed across the electrodes is depicted in FIG. 6. The first three voltages 602, 604, 608 where measured using the 12 cm separation distance and the last voltage 608 was measured using the 16 cm separation distance.

As shown, the first voltage 602 has a resonant frequency of about 3.265 MHz, which correlates to a corrosion potential of −52 mV and corresponds to a directly measured potential of about −43 mV. The second voltage 604 has a resonant frequency of about 3.422 MHz, which correlates to a corrosion potential of −259 mV and corresponds to a directly measured potential of about −249 mV. And, the third voltage 606 has a resonant frequency of about 3.486 MHz, which correlates to a sensor corrosion potential of −344 mV and corresponds to a directly measured potential of about −337 mV.

The fourth voltage 608 was measured at the same time as the second voltage 604 but using a different separation distance—the fourth voltage 608 was measured using a separation distance of 16 cm while the second voltage 604 was measured using a separation distance of 12 cm. As depicted, the amplitude of fourth voltage 608 is less than the amplitude of the second voltage 604. The resonant frequency of each of the second voltage 604 and the fourth voltage 608 are, however, the same, which is about 3.425 MHz, which correlates to a corrosion potential −263 mV and corresponds to a directly measured potential of about −249 mV. In other words, using the system described herein, different separation distances may yield the same results because the system uses resonant frequency as opposed to amplitude.

Figure 7:
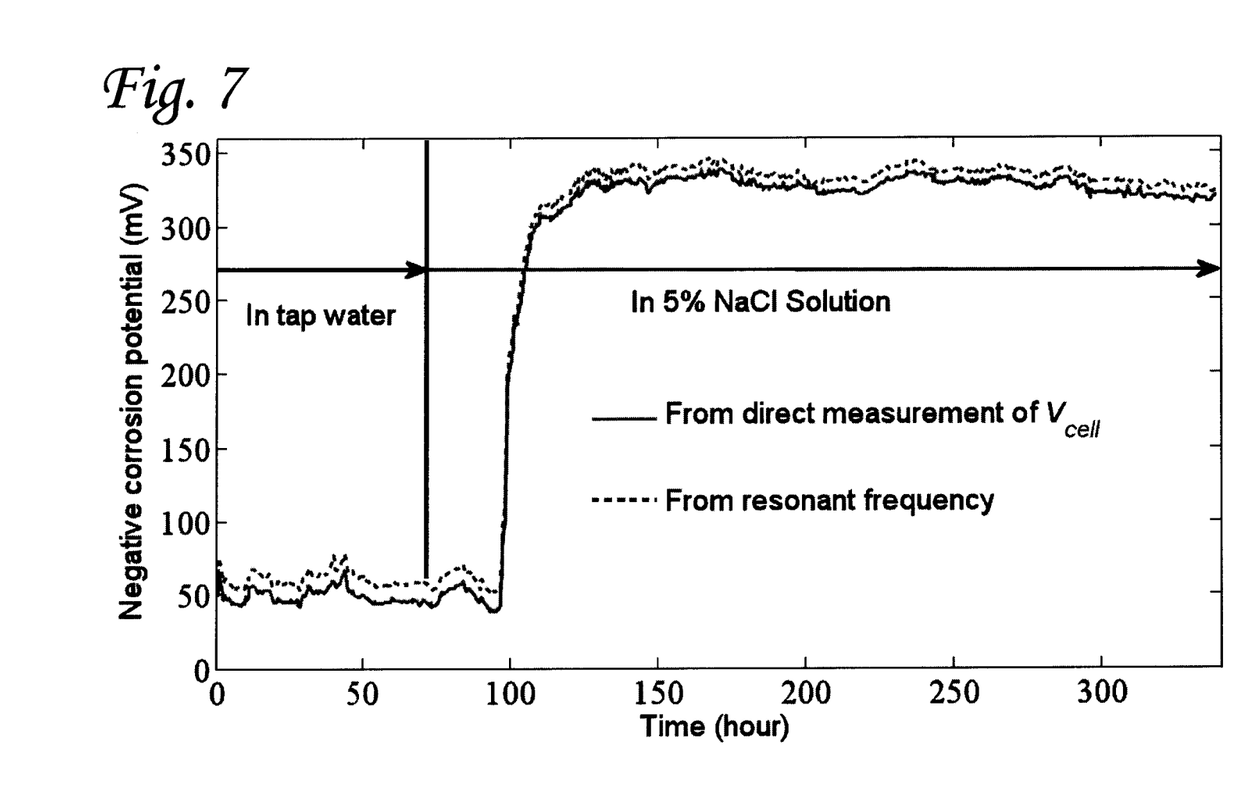
FIG. 7 is a graph of corrosion potential of reinforcement steel over time, e.g., using the exemplary system of FIG. 3 in an experimental setup.

Further, the corrosion potential of reinforcement steel 326 with respect to the reference steel 328 obtained using the sensor's resonant frequency as obtained using interrogator portion 310 and Equation (4) along with the directly measured value for 3 days in water and 11 days in the 5% NaCl solution is depicted in the graph of FIG. 7. The corrosion potential of the reinforcement steel 326 with respect to the reference steel 328 started decreasing about 1 day after submersion in the NaCl solution, which indicated the presence of $Cl^-$ ions inside the mortar specimen at the sensor location (e.g., which may also represent the destruction of the thin passive layer on the reinforcement metal). Further, it can be seen that the directly measured corrosion potentials are around 10 mV greater than the values obtained from the resonant frequency. The possible reasons for the difference may be the finite resistance of the cell, $R_{cell}$ (measured value 0.72 MΩ for $V_{cell}$=−249 mV) rather than the low impedance used in obtaining Equation (4), errors in linear fit used to obtain Equation (4), the precision of the power supply used for the DC calibration, and the 5 mV resolution of the A/D which was used to log cell potential.

The mortar specimen was removed from the NaCl solution after the 11$^{th}$ day, dried for a week, and dissected to expose the sensor portion 320 including the electrodes 326, 328. Rust was found on the surface of the reinforcement steel 326 after the test.

Figure 8:
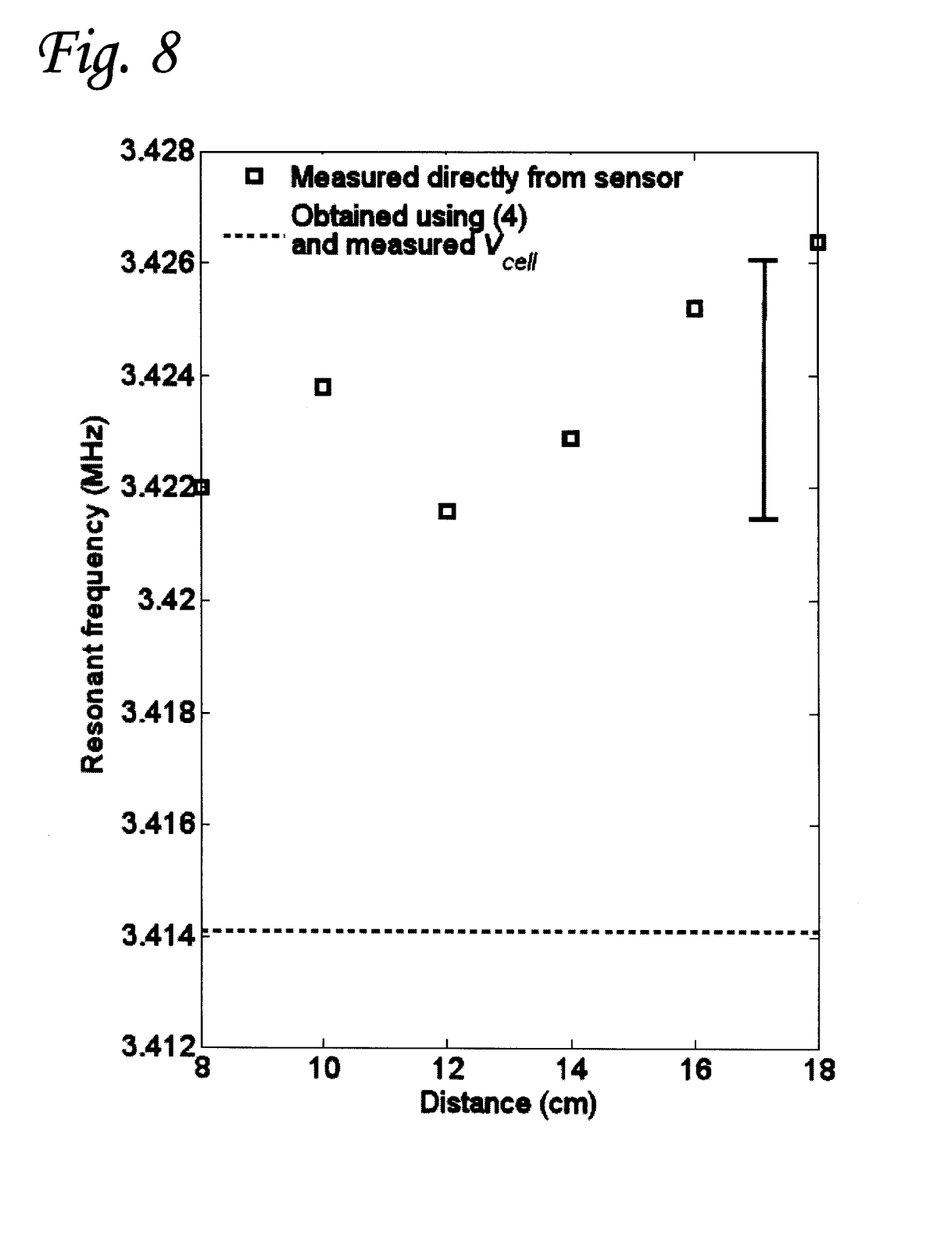
FIG. 8 is a graph of the variation of resonant frequency with respect to separation distance, e.g., using the exemplary system of FIG. 3 in an experimental setup.

As the separation distance between the sensor coil 322 and the interrogator coil 312 increases, the received signal amplitude from the sensor coil 322 may decrease. An experiment was conducted to measure the variation of the resonant frequency of the sensor portion 320 with the separation distance. For each test, the sensor coil 322 was aligned concentrically with the interrogator coil 312. The variation of resonant frequency with distance, when the voltage developed across the electrodes was −249 mV (measured by the A/D), is depicted in FIG. 8. Separation distances between the sensor coil 322 and the interrogator coil 312 less than 8 cm set the varactor in the prototype system in a non-linear operating region, and separation distances greater than about 18 cm provided error greater than 0.14% (corresponding to 6.3 mV) in the prototype system. Further, the separation distance may be improved in other embodiments by increasing the power at the interrogator coil, or by increasing the number of turns and/or radius of the interrogator coil.

In real usage (as opposed to experimental usage), the sensor portion 320 will probably be embedded in concrete structures surrounded by reinforcement steel bars and meshes. Thus, the sensor signal is expected to be reduced with the introduction of these iron objects. The reduction in signal will depend on the density of iron objects and their distance from the sensor, and therefore, when using these types of sensor devices for corrosion monitoring, the placement of the sensor may be important to achieve good sensor signal.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the present disclosure shall not be limiting on the scope of the systems, processes or programs (e.g., the functionality provided by such systems, processes or programs) described herein.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the methods and systems described herein. Various modifications of the illustrative embodiments, as well as additional embodiments of the disclosure, will be apparent upon reference to this description.

What is claimed is:

1. A system for detecting corrosion of metal within material, wherein the system comprises:
    a sensor portion locatable within the material, wherein the sensor portion comprises:
        reinforcement metal,
        reference metal, and
        passive sensing circuitry electrically coupled to the reinforcement metal and the reference metal and configured to measure a potential between the reinforcement metal and the reference metal, wherein the sensing circuitry is further configured to wirelessly transmit a signal representative of a corrosion potential of the reinforcement metal based on the potential between the reinforcement metal and the reference metal when energized, and further wherein the sensing circuitry is configured such that the resonant frequency of the signal representative of the corrosion potential shifts in response to a change in the potential between the reinforcement metal and the reference metal; and
    an interrogator portion locatable outside of the material, wherein the interrogator portion comprises interrogating circuitry configured to wirelessly transmit energy to the sensing circuitry of the sensor portion and to wirelessly receive the signal representative of the corrosion potential from the sensing circuitry of the sensor portion, and further wherein the interrogating circuitry of the interrogator portion is configured to generate one or more corrosion potential values representative of the corrosion potential of the reinforcement metal based on the resonant frequency of the signal representative of the corrosion potential which shifts in response to a change in the potential between the reinforcement metal and the reference metal.

2. The system of claim 1, wherein the interrogator portion is configured to wirelessly transmit energy to the passive sensing circuitry of the sensor portion using a swept frequency source.

3. The system of claim 1, wherein the interrogator portion is configured to wirelessly transmit energy to the passive sensing circuitry of the sensor portion using a time-gated swept frequency source.

4. The system of claim 1, wherein the interrogating circuitry is further configured to wirelessly receive the signal representative of the corrosion potential after a selected period of time has elapsed following energization of the sensor portion by the wirelessly transmitted energy.

5. The system of claim 1, wherein the sensing circuitry is encapsulated by polymer.

6. The system of claim 1, wherein the reinforcement metal comprises steel and the reference metal comprises stainless steel.

7. The system of claim 1, wherein the material is concrete.

8. The system of claim 1, wherein the sensing circuitry of the sensor portion comprises an inductive loop coupled to a capacitor that changes capacitance based on the potential between the reinforcement metal and the reference metal.

9. The system of claim 8, wherein the capacitor comprises a varactor diode.

10. A device for detecting corrosion of metal within material, wherein the device comprises:
    reinforcement metal,
    reference metal, and
    passive sensing circuitry electrically coupled to the reinforcement metal and the reference metal and configured to measure a potential between the reinforcement metal and the reference metal, wherein the sensing circuitry is further configured to wirelessly transmit a signal representative of a corrosion potential of the reinforcement metal based on the potential between the reinforcement metal and the reference metal when energized by an interrogator portion locatable outside of the material, and further wherein the sensing circuitry is configured such that the resonant frequency of the signal representative of the corrosion potential shifts in response to a change in the potential between the reinforcement metal and the reference metal.

11. The device of claim 10, wherein the sensing circuitry is encapsulated by polymer.

12. The device of claim 10, wherein the reinforcement metal comprises steel and the reference metal comprises stainless steel.

13. The device of claim 10, wherein the sensing circuitry of the sensor portion comprises an inductive loop coupled to a capacitor that changes capacitance based on the potential between the reinforcement metal and the reference metal.

14. The device of claim 13, wherein the capacitor comprises a varactor diode.

15. A method of detecting corrosion of metal within material, wherein the method comprises:
   locating a sensor portion within material, wherein the sensor portion comprises:
      reinforcement metal,
      reference metal, and
      passive sensing circuitry electrically coupled to the reinforcement metal and the reference metal and configured to measure a potential between the reinforcement metal and the reference metal, wherein the passive sensing circuitry is further configured to wirelessly transmit a signal when interrogated representative of a corrosion potential of the reinforcement metal based on the potential between the reinforcement metal and the reference metal when energized by an interrogator portion locatable outside of the material, and further wherein the sensing circuitry is configured such that the resonant frequency of the signal representative of the corrosion potential shifts in response to a change in the potential between the reinforcement metal and the reference metal;
   locating an interrogator portion outside of the material proximate the sensor portion;
   wirelessly transmitting energy from the interrogator portion to the sensor portion;
   wirelessly transmitting a signal representative of a corrosion potential of the reinforcement metal from the sensor portion to the interrogator portion based on the potential between the reinforcement metal and the reference metal, wherein the resonant frequency of the signal representative of the corrosion potential shifts in response to a change in the potential between the reinforcement metal and the reference metal; and
   generating one or more corrosion potential values representative of the corrosion potential of the reinforcement metal based on the resonant frequency of the signal representative of the corrosion potential which shifts in response to a change in the potential between the reinforcement metal and the reference metal.

16. The method of claim 15, wherein the method further comprises wirelessly receiving the signal representative of the corrosion potential using the interrogator portion after a selected period of time has elapsed following energization of the sensor portion by the wirelessly transmitted energy.

17. The method of claim 15, wherein the reinforcement metal comprises steel and the reference metal comprises stainless steel.

18. The method of claim 15, wherein the material is concrete.

* * * * *